US006990756B1

(12) United States Patent
Johnson

(10) Patent No.: US 6,990,756 B1
(45) Date of Patent: Jan. 31, 2006

(54) FOOTWEAR ORTHOTIC WITH INSERT

(75) Inventor: Robert Johnson, Fairfield, IA (US)

(73) Assignee: Sylmark Holdings Limited, (IE)

( * ) Notice: Subject to any disclaimer, the term of this patent is extended or adjusted under 35 U.S.C. 154(b) by 0 days.

(21) Appl. No.: 10/996,080

(22) Filed: Nov. 22, 2004

Related U.S. Application Data

(60) Provisional application No. 60/619,184, filed on Oct. 15, 2004.

(51) Int. Cl.
A61F 5/14 (2006.01)
(52) U.S. Cl. .............................. 36/155; 36/159; 36/160
(58) Field of Classification Search .................... 36/91, 36/140, 142–145, 155, 159, 160, 161–164
See application file for complete search history.

(56) References Cited

U.S. PATENT DOCUMENTS

| 3,543,765 | A | | 12/1970 | Alzner |
| 4,739,765 | A | | 4/1988 | Sydor et al. |
| 4,742,625 | A | | 5/1988 | Sydor et al. |
| 4,813,157 | A | | 3/1989 | Boisvert et al. |
| 5,040,313 | A | | 8/1991 | Simjian et al. |
| 5,052,130 | A | | 10/1991 | Barry et al. |
| 5,138,774 | A | * | 8/1992 | Sarkozi ........................ 36/164 |
| 5,191,727 | A | | 3/1993 | Barry et al. |
| 5,203,793 | A | | 4/1993 | Lyden |
| 5,315,769 | A | | 5/1994 | Barry et al. |
| 5,772,945 | A | | 6/1998 | Brown |
| 5,952,065 | A | | 9/1999 | Mitchell et al. |
| 5,960,566 | A | | 10/1999 | Brown |
| 5,996,254 | A | | 12/1999 | Goven |
| 6,205,685 | B1 | * | 3/2001 | Kellerman ........................ 36/44 |
| 6,269,555 | B1 | | 8/2001 | Brown |
| 6,301,807 | B1 | * | 10/2001 | Gardiner ........................ 36/155 |
| 6,381,875 | B2 | | 5/2002 | Singer et al. |
| 6,393,736 | B1 | | 5/2002 | Greer, Jr. et al. |
| 6,477,791 | B2 | | 11/2002 | Luthi et al. |
| 6,521,305 | B1 | | 2/2003 | Mitchell et al. |
| 6,557,273 | B2 | | 5/2003 | Polifroni |
| D475,184 | S | | 6/2003 | Polifroni |
| 6,594,922 | B1 | | 7/2003 | Mansfield et al. |
| 6,598,319 | B2 | | 7/2003 | Hardt |
| D485,425 | S | | 1/2004 | Polifroni |
| 6,732,457 | B2 | * | 5/2004 | Gardiner ........................ 36/155 |
| 2002/0050080 | A1 | | 5/2002 | Vasyli |
| 2002/0083618 | A1 | | 7/2002 | Erickson et al. |
| 2003/0009915 | A1 | | 1/2003 | Bacon |
| 2004/0003514 | A1 | | 1/2004 | Cole |

* cited by examiner

Primary Examiner—Ted Kavanaugh
(74) Attorney, Agent, or Firm—Kathy Mojibi Kavcioglu

(57) ABSTRACT

A footwear orthotic is disclosed having a plurality of removable inserts. The removable inserts are preferably provided in the metatarsal region and/or in the heel region. The inserts are designed to gradually train the user's feet to become comfortably accustomed to orthotic support. Each insert preferably has a different profile than the others. The user can select the insert with the most appropriate profile and securely position the insert in the footwear orthotic for use.

8 Claims, 3 Drawing Sheets

FOOTWEAR ORTHOTIC WITH INSERT

This application claims the benefit of Provisional 60/619,184 filed Oct. 15, 2004.

FIELD OF INVENTION

The present invention relates generally to footwear orthotics and more particularly to footwear orthotics having removable inserts.

BACKGROUND OF THE INVENTION

During their lifetime, it is reported that most people will have foot problems of sufficient importance to cause discomfort and/or pain. Most minor foot problems are discussed with amateurs, such as shoe salespersons. More serious problems are referred to primary care physicians or orthopedists. Ideally, pedorthic management begins with an evaluation of footwear and foot support. Regardless of whether a foot problem is minor or substantial, the foot and shoe must work together as a unit, with the shoe providing proper alignment and support of the foot.

Where it is found that a person is not receiving the proper alignment and support from his or her footwear, orthotics can be used in conjunction with the footwear to provide the support needed. Orthotics are typically inserted into the person's shoes, and therefore are also referred to as "orthotic inserts." The terms orthotics and orthotic inserts are used interchangeably herein.

One advantage of using orthotics is to augment the arch support provided by footwear. Lack of sufficient arch support leads to numerous foot problems. For example, lack of support in the medial arch (the main arch along the inside of the foot) can lead to foot fatigue, plantar fasciitis (heel spurs), neuroma pain, or bunions. Lack of support in the metatarsal arch (under the ball of the foot) can cause metatarsalgia (a pain in the ball of the foot), pain in the toes, or decreased balance control. Orthotics have been developed to deal with each of these problems, either individually or in combination.

A proper orthotic should provide support for both the metatarsal arch and the plantar arch simultaneously. A typical problem in developing orthotics is the difficulty in balancing the need for proper arch support with the comfort of the user. In one known type of orthotics, a soft, "cushion-type" pad is provided. Although the orthotic pad has an initial contour to provide arch support, it is too soft to maintain support during wear. Accordingly, under the weight of the user, the orthotic pad ultimately conforms to the shape of the foot rather than vice versa, and as a result, fails to provide adequate support to the wearer.

To overcome the shortcomings of the orthotic pads described above, other known orthotics have been made of rigid materials (such as hard plastics). A disadvantage of the rigid, relatively hard orthotics is that, initially, they can be uncomfortable for the user. The rigid orthotic typically has a contoured upper portion that applies pressure to (and thus supports) the foot arches. Users unaccustomed to the constant pressure applied by the rigid orthotic may find it irritating. The arch support, although ultimately helpful in the treatment of foot problems described above, is initially difficult to wear due to the user's unfamiliarity with arch support products. The pressure applied by the protrusions in the orthotic can lead to acute irritation or, in some instances, calluses.

As a result of the discomfort, some users may stop wearing orthotics altogether and abandon their treatment program, thereby failing to obtain proper treatment and possibly escalating their foot problems.

It is therefore desirable to provide an orthotic that is sufficiently rigid so as to provide adequate arch support, yet comfortable in use.

DETAILED DESCRIPTION OF PREFERRED EMBODIMENTS

Figure 1:
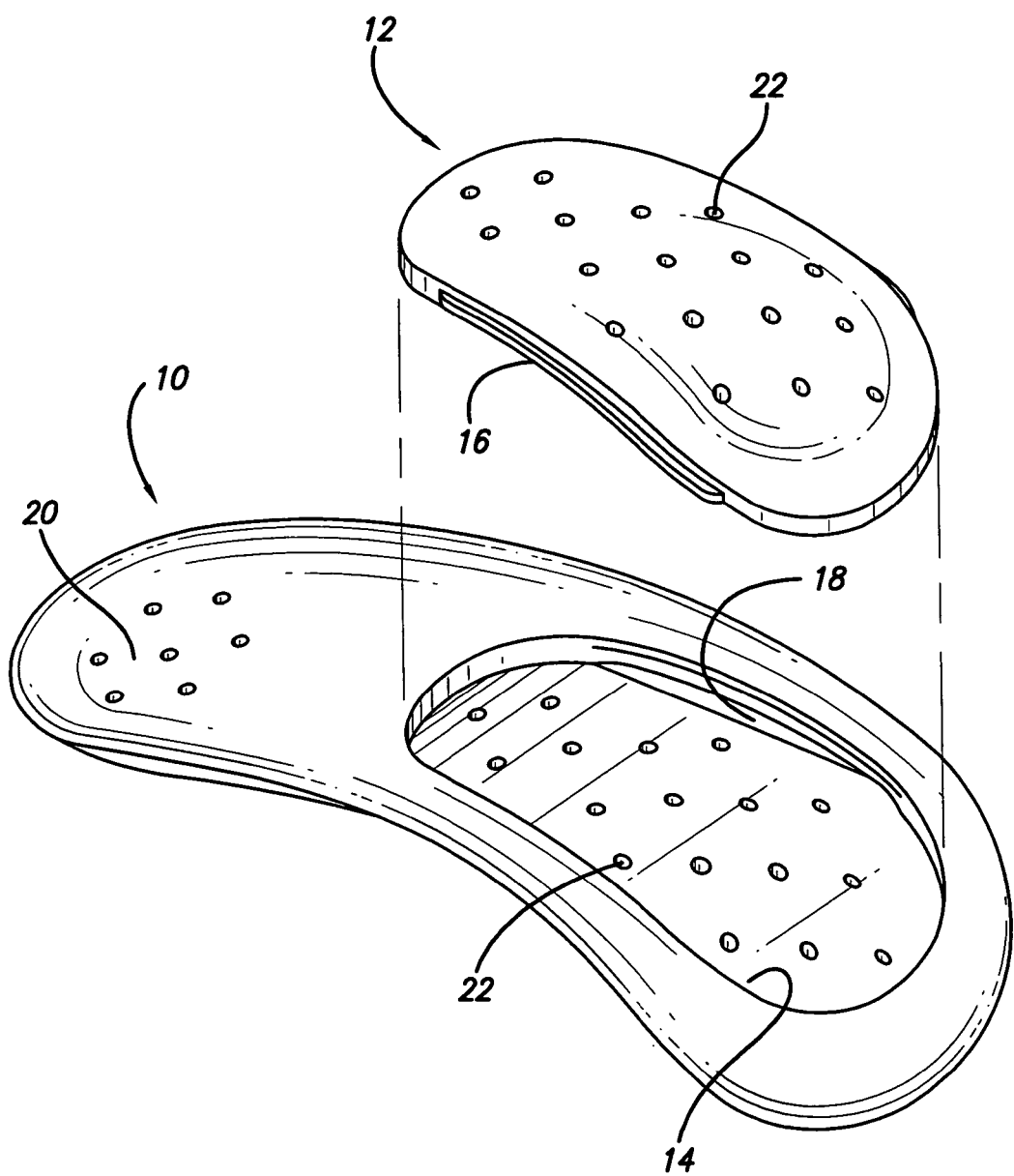
FIG. 1 is an exploded view of a preferred embodiment of footwear orthotic of the present invention with a removable insert.
Figure 2:
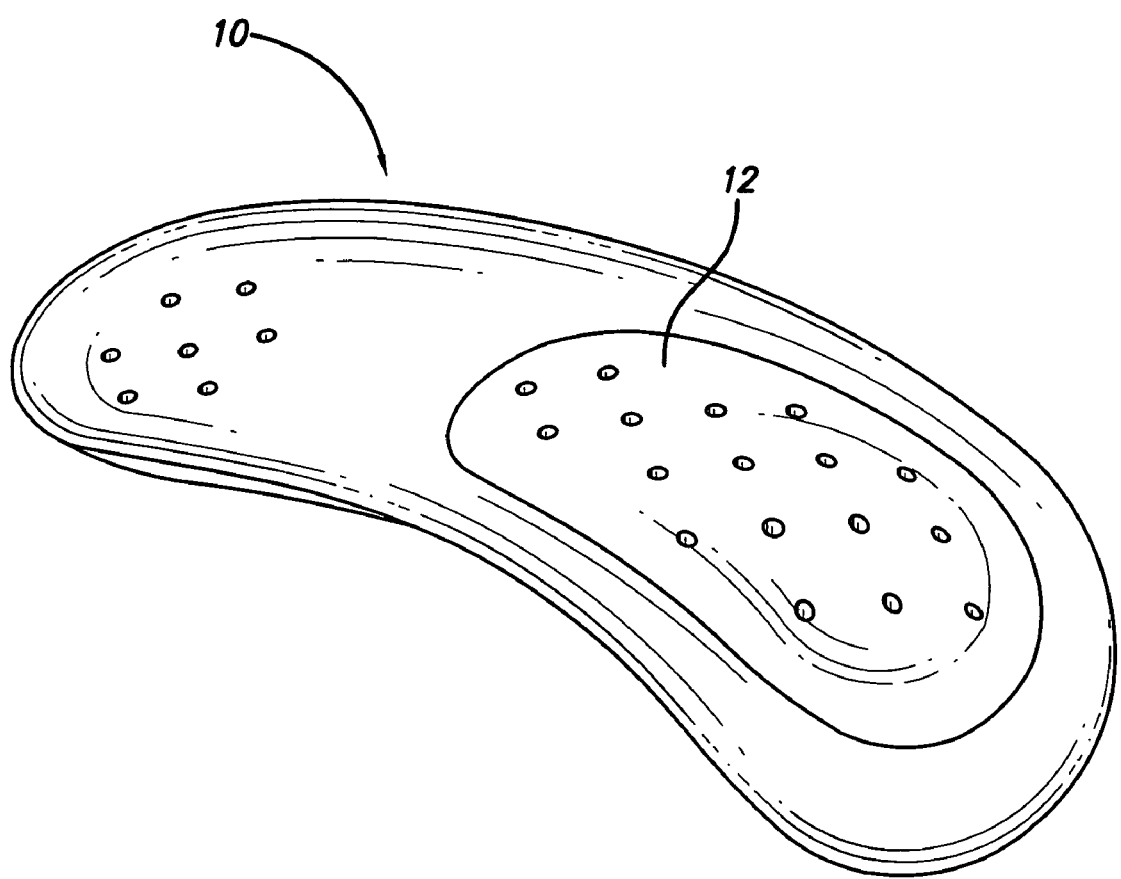
FIG. 2 is a perspective view of a preferred embodiment of the footwear orthotic of the present invention showing the removable insert installed therein.

As shown in FIG. 1, in a preferred embodiment of the present invention, the footwear orthotic 10 includes a removable insert 12. FIG. 1 shows the insert 12 removed from the orthotic 10, while FIG. 2 shows the insert installed therein. As will be described in greater detail below, the removable insert 12 enables a user to customize an orthotic for a specified comfort level and gradually train his or her foot to become accustomed to the maximum arch support provided by an orthotic.

The orthotic is preferably constructed of a single piece of molded resilient plastic so shaped as to include protrusions and contours for providing proper arch support. The specific shape of the orthotic may vary according to the size of the user's feet. One skilled in the art will be able to practice the present invention with orthotics of various sizes and shapes.

As discussed above, most orthotic wearers complain that the pressure applied by the orthotic contours, particularly in the metatarsal area, is initially uncomfortable. Thus, it is desirable to, at least in the beginning stages, soften the metatarsal region. The present invention enables the users to achieve the appropriate comfort level by selecting the level of arch support that is appropriate for them.

Figure 3:
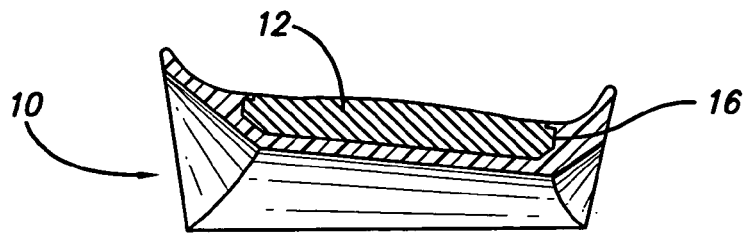
FIG. 3 is a cross-sectional view of a preferred embodiment of the footwear orthotic of the present invention as having a low-profile insert installed therein.
Figure 4:
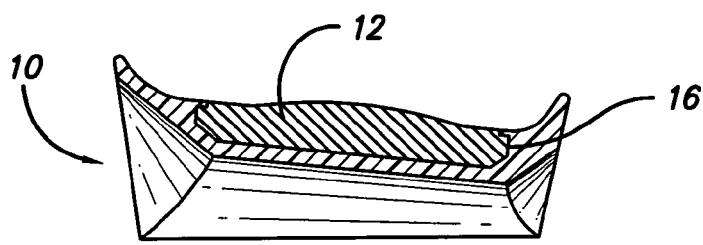
FIG. 4 is a cross-sectional view of a preferred embodiment of the footwear orthotic of the present invention as having a medium-profile insert installed therein.
Figure 5:
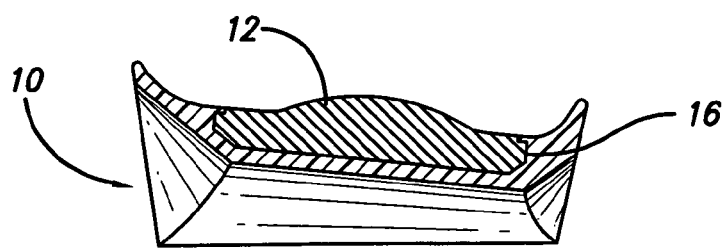
FIG. 5 is a cross-sectional view of a preferred embodiment of the footwear orthotic of the present invention as having a high-profile insert installed therein.

FIGS. 3 through 5, show inserts 12 having varying degrees of arch support. For example, of the inserts shown in FIGS. 3 through 5, the insert shown in FIG. 3 has the lowest profile. It is the flattest in terms of height and is probably the most comfortable for someone who is not accustomed to wearing footwear orthotics. While the insert in FIG. 3 provides the most comfort, it provides the least arch support. The purpose of this initial stage insert is to train the user to become accustomed to the wear of orthotics, gradually.

Once the user is comfortable with the use of the initial stage insert, he or she can proceed to the next level. The insert 12 shown in FIG. 4 has a higher profile than that shown in FIG. 3. There is a more pronounced protrusion near the center of the insert. By replacing the initial stage insert (shown in FIG. 3), with the insert shown in FIG. 4, the user can benefit from increased arch support in a gradual increment.

At each stage, when the user has become comfortable in wearing that stage's orthotic and has grown accustomed to the pressure applied by the removable insert of that stage's orthotic, he or she can progress to the next level orthotic, until the user reaches the level of an orthotic having the maximum arch support. A preferred embodiment of an orthotic with maximum arch support is shown in FIG. 5. The removable insert, shown in FIG. 5, has a more pronounced protrusion than that shown in FIG. 3 or 4. Because the orthotic wearer has become accustomed to the orthotics shown in FIGS. 3 and 4 when he or she tries the orthotic shown in FIG. 5, it should be much more comfortable for the user.

In a preferred embodiment of the invention, as shown in FIGS. 3 through 5, orthotic 10 is provided with a set of three removable inserts 12, each having a higher profile arch than the last. The number of orthotics in a set, and the degree to which the profile of each arch increases may vary. In one embodiment of the invention, the arch of the initial insert is 25% or lower than the size of the arch of the insert with the maximum arch support, and the arch of the medium-level profile is 50% or lower than the size of the arch of the insert with the maximum arch support.

The present invention enables a user to customize the arch support provided by an orthotic. Furthermore, the user can train his or her feet to gradually grow accustomed to a maximum level arch support. By providing a removable insert, the need to purchase multiple orthotics having different size protrusions is eliminated.

In a preferred embodiment of the invention, as shown in FIGS. 1 and 3–5, the removable insert 12 is press-fitted or friction fitted into a cavity 14 in the orthotic 10. The cavity 14 is dimensioned to securely receive the insert 12. To ensure that the insert 12 remains in place, the insert 12 preferably has a rail 16 positioned on each side. Rail 16 engages a corresponding guide 18 in the cavity 12, to hold the insert in position. Other known means of retaining the removable insert in the cavity may be used.

In another preferred embodiment of the invention (not shown in the drawings), the heel portion 20 comprises a removable insert. In a manner similar to that described above, the orthotic can be provided with removable heel inserts having various degrees of hardness and thickness. Furthermore, the inserts can have different contours. As with the metatarsal inserts, the heel inserts would be positioned in a cavity dimensioned to securely receive the heel insert. The heel inserts can be maintained in the cavity in the same manner as described with respect to the metatarsal inserts.

The inserts and the orthotic preferably include apertures 22 to facilitate air circulation through the orthotic. The aperture 22 and cavity 14 are preferably dimensioned to achieve the desired flexibility.

Many modifications and other embodiments of the invention set forth herein will come to mind to one skilled in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method of acclimating a user to a footwear orthotic with maximum arch support, comprising the steps of:
   providing a rigid orthotic configured to receive a removable insert;
   providing a training insert and a final insert, wherein the cross-sectional height of the training insert is smaller than the cross-sectional height of the final insert;
   press-fitting the training insert into the orthotic, wherein the orthotic retains the insert therein for a selected time period; and
   replacing the training insert with the final insert at the end of the selected time period, wherein the final insert is press-fitted into the orthotic.

2. The method of claim 1 further comprising an intermediate insert, wherein the training insert has a cross-sectional height that is 0–25% of the cross-sectional height of the final insert, wherein the intermediate insert has a cross-sectional height that is 26–50% of the cross-sectional height of the final insert, wherein the training insert is replaced by the intermediate insert at the end of the selected time period and wherein the intermediate insert is replaced by the second insert after a second preselected time period.

3. The method of claim 1 wherein the orthotic comprises a resilient plastic.

4. The method of claim 1 wherein the orthotic comprises a single-piece resilient plastic.

5. The method of claim 1 wherein the orthotic comprises an opening dimensioned to frictionally retain the insert therein.

6. A method of acclimating a user to a footwear orthotic with maximum arch support, comprising the steps of:
   providing a rigid orthotic configured to receive a removable insert, wherein the orthotic frictionally retains the removable insert therein;
   providing a training insert and a final insert, wherein the cross-sectional height of the training insert is smaller than the cross-sectional height of the final insert;
   press-fitting the training insert into the orthotic, wherein the orthotic retains the insert therein for a selected time period; and
   replacing the training insert with the final insert at the end of the selected time period.

7. A method of acclimating a user to a footwear orthotic with maximum arch support, comprising the steps of:
   providing a rigid orthotic configured to receive a removable insert, the orthotic defining an opening therein, wherein the opening is dimensioned to frictionally retain the insert therein when the insert is press-fitted into the opening;
   providing a training insert and a final insert, wherein the cross-sectional height of the training insert is smaller than the cross-sectional height of the final insert;
   press-fitting the training insert into the orthotic, wherein the orthotic retains the insert therein for a selected time period; and
   replacing the training insert with the final insert at the end of the selected time period.

8. The method of claim 7 wherein each of the training insert and the final insert have a lip extending therefrom, and the lip is dimensioned to be receved by a guide in the opening of the orthotic.

* * * * *